United States Patent
Zhang et al.

(10) Patent No.: US 6,680,344 B1
(45) Date of Patent: Jan. 20, 2004

(54) METHOD OF TREATING HAIR LOSS USING DIPHENYLMETHANE DERIVATIVES

(75) Inventors: Lixin Lilly Zhang, Cincinnati, OH (US); Robert Scott Youngquist, Mason, OH (US)

(73) Assignee: The University of Texas Southwestern Medical Center, Dallas, TX (US)

( * ) Notice: Subject to any disclaimer, the term of this patent is extended or adjusted under 35 U.S.C. 154(b) by 0 days.

(21) Appl. No.: 09/980,407

(22) PCT Filed: Mar. 1, 2000

(86) PCT No.: PCT/US00/05254

§ 371 (c)(1),
(2), (4) Date: Mar. 29, 2002

(87) PCT Pub. No.: WO00/72813

PCT Pub. Date: Dec. 7, 2000

Related U.S. Application Data
(60) Provisional application No. 60/137,024, filed on Jun. 1, 1999.

(51) Int. Cl.⁷ .............................................. A61K 31/192
(52) U.S. Cl. ....................................................... 514/571
(58) Field of Search .......................................... 514/571

(56) References Cited

U.S. PATENT DOCUMENTS

| | | | |
|---|---|---|---|
| 3,530,146 A | 9/1970 | Newman et al. | 260/330.5 |
| 3,616,237 A | 10/1971 | Newman et al. | 195/80 |
| 4,323,691 A | 4/1982 | Ours et al. | 560/36 |
| 4,425,404 A | 1/1984 | Suzuki et al. | 428/341 |
| 4,683,241 A | 7/1987 | Miyano et al. | 514/412 |
| 4,711,855 A | 12/1987 | Feinberg | 436/500 |
| 5,061,798 A | 10/1991 | Emmett et al. | 544/239 |
| 5,284,971 A | 2/1994 | Walker | 562/429 |
| 5,401,772 A | 3/1995 | Yokoyama | 514/539 |
| 5,569,674 A | 10/1996 | Yokoyama | 514/539 |
| 5,580,722 A | 12/1996 | Foulkes et al. | 435/6 |
| 5,654,468 A | 8/1997 | Yokoyama | 560/43 |
| 5,773,663 A | 6/1998 | Curtze et al. | 568/333 |
| 5,807,820 A | 9/1998 | Elias | 514/11 |
| 5,883,294 A | 3/1999 | Scanlan et al. | 562/471 |
| 6,174,925 B1 | 1/2001 | Bailey et al. | 514/646 |
| 6,221,911 B1 | 4/2001 | Lavin et al. | 514/567 |

FOREIGN PATENT DOCUMENTS

| | | |
|---|---|---|
| AT | 388372 | 6/1989 |
| CA | 1179269 | 12/1984 |
| DE | 1617477 | 1/1970 |
| DE | 2014514 | 10/1970 |
| DE | 4214313 | 11/1992 |
| DE | 4405469 | 8/1995 |
| EP | 51023 | 5/1982 |
| EP | 0123528 | 10/1984 |
| EP | 188248 | 7/1986 |
| EP | 243956 | 11/1987 |
| EP | 251315 | 1/1988 |
| EP | 0360701 | 3/1990 |
| EP | 0371484 | 6/1990 |
| EP | 0379935 | 8/1990 |
| EP | 0454165 | 10/1991 |
| EP | 498707 | 8/1992 |
| EP | 0580550 | 1/1994 |

(List continued on next page.)

OTHER PUBLICATIONS

Berman, et al., Peripheral Effects of L–Thyroxine on Hair Growth and Coloration in Cattle, J. Endocrin 20:288–292 (1960).

Gunaratnam, et al., The Journal of Small Animal Practice, (1986), pp. 17–29, vol. 27, No. 1.

Hale, et al., The Journal of Experimental Zoology, (1975), pp. 49–62, 191.

N Yokoyama: "Synthesis and structure activity relationships of oxamic acid and acetic acid derivatives related to L–thronine" Journal of Medicinal Chemistry, US, American Chemical Society, Washington, vol. 38, No. 4, 1995, pp. 695–707.

Yamamoto et al., "Hair Growth–Stimulating Effects of Cyclosporin A and Fk506, Potent Immunosuppressants", Journal of Dermatological Service, vol. 7 (suppl.), pp. S47–S54 (1994).

Mauer et al., "Hair Growth Modulation by Topical Immunophilin Ligands", American Journal of Pathology, vol. 150, No. 4, pp. 1433–1441 (Apr. 1997).

Paus et al., Hair Growth Control by Immunosuppression:, Archives of Dermatological Research, vol. 288, No. 7, pp. 408–410 (1996).

(List continued on next page.)

*Primary Examiner*—Phyllis G. Spivack

(57) ABSTRACT

The present invention relates to a method of treating hair loss comprising administering a composition having a cardiac-sparing compound characterized by the structure:

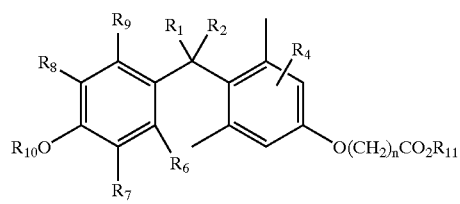

and pharmaceutically acceptable salts, hydrates, and biohydrolyzable amides, esters, and imides thereof. In this compound, n may be an integer from 1 to 3; $R_1$ and $R_2$ may each, independently, be a hydrogen or lower alkyl; $R_4$ may be hydrogen, lower alkyl or cycloalkyl; $R_6$ and $R_9$ may each, independently, be hydrogen or lower alkyl; $R_7$ and $R_8$ may each, independently, be hydrogen, lower alkyl, substituted phenyl, or substituted benzyl; $R_{10}$ may be hydrogen, lower alkyl, cycloalkyl, or acyl; and $R_{11}$ may be hydrogen, lower alkyl, or cycloalkyl.

11 Claims, No Drawings

FOREIGN PATENT DOCUMENTS

| | | |
|---|---|---|
| EP | 0749752 | 12/1996 |
| EP | 810218 | 12/1997 |
| FR | 2543434 | 10/1984 |
| FR | 2755965 | 5/1998 |
| GB | 859546 | 10/1968 |
| GB | 2138286 | 10/1984 |
| JP | 59041343 | 3/1984 |
| JP | 61165311 | 7/1986 |
| JP | 62150245 | 7/1987 |
| JP | 63146845 | 6/1988 |
| JP | 63279246 | 11/1988 |
| JP | 2300148 | 12/1990 |
| JP | 4052646 | 2/1992 |
| JP | 04368379 | 12/1992 |
| JP | 4368379 | 12/1992 |
| JP | 6172340 | 6/1994 |
| JP | 7149614 | 6/1995 |
| JP | 8092082 | 4/1996 |
| JP | 8267922 | 10/1996 |
| JP | 8267932 | 10/1996 |
| JP | 8277243 | 10/1996 |
| JP | 10133427 | 5/1998 |
| JP | 10158382 | 6/1998 |
| PL | 119115 | 11/1981 |
| PL | 138940 | 11/1986 |
| WO | 9101379 | 2/1991 |
| WO | 9212635 | 8/1992 |
| WO | 9420062 | 9/1994 |
| WO | WO 9420062 | 9/1994 |
| WO | WO 96/25943 | 8/1996 |
| WO | 9625943 | 8/1996 |
| WO | WO 9707790 | 3/1997 |
| WO | WO 9857919 | 12/1998 |
| WO | 9857919 | 12/1998 |
| WO | 0000468 | 1/2000 |

OTHER PUBLICATIONS

Paus et al., "Cyclosporin A, PSC 833 and FK 506, but not Cyclosporin H and Rapamycin, Induce Anagen and Inhibit Catagen in Murine Skin", The Journal of Investigative Dermatology, vol. 101, No. 3, p. 420 (1993).
Paus et al., "Cyclosporin A, FK 506 and Related Drugs as Tools for Hair Research", Archives of Dermatological Research, vol. 285, Nos. 1–2, p. 80 (1993).
Traber et al., "Cyclosporins—New Analogues by Precursor Directed Biosyntheses", The Journal of Antibiotics, vol. 42, No. 4, pp. 591–597 (1989).
Vinod. K. Sharma et al: "Evaluation of thyroid function in North Indians with alopecia areta: Response to intravenous injection of 100microgram thyrotropin releasing hormone (TRH)", vol. 26, No. 6, pp. 339–342 (1999).
Yoshihara, et al., Bioorg. Med. Chem. (1998), pp. 1179–1183, 6 (8).
Chiellini, et al., Chem. Biol. (1998), pp. 299–306, 5 (6).
Ji, et al., Yaoxue Xuebao (1998), pp. 72–74, 33 (1).
Krumm, et al., Inorg. Chem. (1997), pp. 5222–5230, 36 (23).
Kuroda, et al., Chem. Pharm. Bull, (1997), pp. 678–684, 45 (4).
Kuroda, et al., J. Org. Chem. (1996), pp. 9560–9563, 61 (26).
Iwasaki, et al., Chem. Pharm. Bull. (1995), pp. 1701–1705, 43 (10).
Yasuda, et al., Mokuzai Gakkaishi (1986), pp. 51–58, 32 (1).
Keay, et al., Can. J. Chem. (1983), pp. 1987–1995, 61 (9).
Bogoslovskii, et al., Org. Khim. (1976), pp. 39–43. Gor'kogo, Perm. USSR.
Lapkin, et al., Zh. Org. Khim. (1972), pp. 292–293, 8 (2).
Vasilevskaya, et al., Zh. Org. Khim. (1970), pp. 126–132, 6 (1).
Dembri, et al., Mol. Cell. Endocrinol. (1984), pp. 223–232, 37 (2).
Cody, et al., Acta Crystallogr., Sect. B (1982), pp. 2270–2272, B38 (8).
Ito, et al., Chem. Pharm. Bull, (1997), pp. 1403–1413, 45 (9).
Mercer, et al., Polymer (1997), pp. 1989–1995, 38 (8).
Goodwin, et al., Macromolecules (1997), pp. 2767–2774, 30 (9).
Krumm, et al., Inorg. Chem. (1997), pp. 366–381, 36 (3).
Nishida, et al., Inorg. Chem. (1995), pp. 6085–6092, 34 (24).
Verma, et al., Nat. Prod. Lett. (1994), pp. 105–110, 5 (2).
Mehta, et al., Tetrahedron (1994), pp. 11729–11742, 50 (40).
Fletcher, et al., Organohalogen Compd. (1993), 12 (Dioxin '93, 13th International Symposium on Chlorinated Dioxins and Related Compounds, 1993), pp. 103–106.
Minami, et al., Phytochemistry (1994), pp. 501–506, 36 (2).
Lin, et al., J. Pharm. Sci. (1992), pp. 1109–1112, 81 (11).
Singh, et al., Pol. J. Chem. (1992), pp. 469–475, 66 (3).
Elix, et al., Aust. J. Chem. (1991), pp. 1157–1162, 44 (8).
Elix, et al., Aust. J. Chem. (1990), pp. 1591–1595, 43 (9).
Elix, et al., Aust. J. Chem, (1990), pp. 1291–1295, 43 (7).
Horne, et al., J. Org. Chem. (1990), pp. 4520–4522, 55 (15).
Birkbeck, et al., Aust. J. Chem. (1990), pp. 419–425, 43 (2).
Pulgarin, et al., Helv Chim. Acta (1989) pp. 1061–1065, 72 (5).
Aurell, et al., J. Nat. Prod. (1989), pp. 852–857, 52 (4).
Comber, et al., J. Chem. Soc., Perkin Trans. 1 (1989), pp. 441–448, (3).
Sant'ana, et al., F.E.C.S. Int. Conf. Chem. Biotechnol. Biol. Act. Nat. Prod., [Proc.] 3rd (1987), Meeting Date 1985, vol. 4, pp. 363–366.
Gil, et al., J. Nat. Prod. (1988), pp. 339–343, 51 (2).
Sannicolo, Gazz. Chim. Ital. (1985), pp. 91–95, 115 (2).
Kellman, et al., ACS Symp. Ser. (1987), 326 (Phase Transfer Catal.: New Chem., Catal., Appl.), pp. 128–142.
Fujii, et al., J. Biochem. (Tokyo) (1987), pp. 11–18, 101 (1).
Oda, et al., Chem. Pharm. Bull. (1986), pp. 858–863, 34 (2).
Guzinger, et al., Helv. Chim. Acta (1985), pp. 1940–1947, 68 (7).
Ahluwalia, et al., Monatsh. Chem. (1985), pp. 869–872, 116 (6–7).
Pulgarin, et al., Helv. Chim. ACTA (1985), pp. 945–948, 68 (4).
Plattner, et al., Diuretics: Chem., Pharmacol., Clin. Appl., Proc. Int. Conf. Diuretics, 1st (1984), pp. 21–29.
Tanaka, et al., Chem. Pharm. Bull. (1984), pp. 2676–2686, 22 (7).
Dembri, et al., Mol. Cell. Endocriniol (1984), pp. 223–232, 37 (2).
Mahandru, et al., J. Chem. Soc., Perkin Trans. 1 (1983), pp. 2249–2251, (9), pp. 413–416, (2).
Ruminski, Chem. Ber. (1983), pp. 970–979, 116 (3).
Cody, Acta Crystallogr, Sect. B (1982), B38(8), 2270–2272.
Shapiro, et al., J. Protozool. (1982), pp. 85–90, 29 (1).
Malhotra, et al., Indian J. Chem., Sect. B (1982), pp. 107–108, 21B (2).
Baslas, et al., Acta Cienc. Indica, [Ser.] Chem. (1981), pp. 31–34, 7 (1–4).
Sargent, J. Chem. Soc., Perkin Trans. 1 (1982), pp. 403–411, (2).

Cullen, et al., Aust. J. Chem. (1981), pp. 2701–2703, 34 (12).
Fujita, et al., Phytochemistry (1981), pp. 2183–2185, 20 (9).
Correa, et al., Phytochemistry (1981), pp. 305–307, 20 (2).
McEwen, et al., J. Chem. Soc., Perkin Trans. 1 (1981), pp. 883–886, (3).
Sala, et al., J. Chem. Soc., Perkin Trans. 1 (1981), pp. 887–882, (3).
Finlay–Jones, et al., J. Chem. Soc., Perkin Trans. 1 (1981), pp. 874–876, (3).
Sala, et al., J. Chem. Soc., Perkin Trans. 1 (1981), pp. 855–869, (3).
Cotterill, et al., J. Chem. Soc., Perkin Transd. 1 (1980), pp. 2353–2357, (11).
Danilenko, et al., Izv. Akad. Nauk SSSR, Ser. Khim. (1980), pp. 1606–1611, (7).
Fujita, et al., Chem. Pharm. Bull. (1980), pp. 2482–2486, 28 (8).
Fitzpatrick, et al., J. Chem. Soc., Perkin Trans. 1 (1980), pp. 85–89, (1).
Sundholm, Acta Chem. Scand., Ser. B (1979), pp. 475–482, B33 (7).
Sato, et al., Symp. Pap.—IUPAC Int. Symp. Chem. Nat. Prod., 11th (1978), vol. 1, pp. 175–178.
Andreev, et al., Izv. Sib. Otd. Akad. Nauk SSR, Ser. Tekh. Nauk (1979), pp. 124–129, (2).
Baslas, et al., Curr. Sci. (1979, pp. 814–815, 48 (18).
Zharkova, et al., Rev. Phys. Appl. (1979), pp. 555–558, 14 (4).
Avnir, et al., J. Chem. Soc., Chem. Commun. (1978), pp. 1109–1110, (24).
Sala, et al., J. Chem. Soc., Chem. Commun. (1978), pp. 1043–1044, (23).
Feringa, et al., Bioorg. Chem. (1978), pp. 397–498, 7 (4).
Sato, et al., Tennen Yuki Kagobutsu Toronkai Koen Yoshishu, 21st (1978), pp. 152–158; Publisher Hokkaido Daizku, Sapporo, Japan.
Sundholm, Tetrahedron (1978), pp. 577–586 34 (5).
Prashad, et al., Indian J. Chem., Sect. B (1978), pp. 142–143, 16B (2).
Sato, et al., J. Chem. Soc., Chem. Commun. (1978), pp. 135–136, (3).
Feringa, et al., Tetrahedron Lett. (1977), pp. 4447–4450, (50).
Djura, et al., J. Chem. Soc., Perkin Trans. 1 (1978), pp. 395–400, (4).
Broadhurst, et al., J. Chem. Soc., Perkin Trans. 1 (1977), pp. 2502–2512, (22).
Fujita, et al., Tetrahedron Lett. (1977), pp. 4503–4506, (51).
Schweppe, Mikrochim. Acta (1977), pp. 583–596, 2 (5–6).
Ueda, et al., Bull. Chem. Soc. Jpn. (1977), pp. 193–196, 50 (1).
Sargent, et al., Aust. J. Chem. (1976), pp. 2263–2269, 29 (10).

Harris, J. Am. Chem. Soc. (1976), pp. 5380–5386, 98 (17).
Sargent, et al., Aust. J. Chem. (1976), pp. 907–914, 29 (4).
Chevolot–Magueur et al., Phytochemistry (1976), pp. 767–771, 15 (5).
Holloway, et al., Phytochemistry (1975), pp. 2517–2518, 14 (11).
Owen, et al., J. Chem. Soc., Perkin Trans. 1 (1975) pp. 1380–1386, (14).
Kroeller, Mitteilungsbl. GDCH–Fachgruppe Lebensmittelchem. Gerichtl. Chem. (1975), pp. 181–182, 29 (5).
Ghosal, et al., J. Chem. Soc., Perkin Trans. 1 (1974), pp. 2538–2541, (22).
Hassall, et al., J. Chem. Soc., Perkin Trans. 1 (1973), pp. 2853–2861, (23).
Sargent, Can. J. Chem. (1973), pp. 4088–4089, 51 (24).
Quillinan, et al., J. Chem. Soc., Perkin Trans. 1 (1973), pp. 1329–1337, (13).
Hendrickson, et al., J. Amer. Chem. Soc. (1972), pp. 6834–6843, 94 (19).
Koch, Angew. Makromol. Chem. (1971), pp. 21–33, 20.
Isaka, et al., Yakugaku Zasshi (1971), pp. 1027–1029, 91 (9).
Lubenets, et al., Zh. Org. Khim. (1971), pp. 805–812, 7 (4).
Newman, J. Heterocycl. Chem. (1970), pp. 957–958, 7 (4).
Lubenets, et al., Zh. Org. Khim. (1970), pp. 365–368, 6 (2).
Sargent, et al., J. Chem. Soc. C (1969), pp. 2763–2767, (19).
Findlay, et al., J. Chem. Soc. C (1969), pp. 2761–2762, (19).
Newman, J. Org. Chem. (1969), pp. 1463–1465, 34 (5).
Lauer, et al., Chem. Ber. (1969), pp. 1631–1640, 102 (5).
Kamikura, Shokuhin Eiseigaku Zasshi (1968), pp. 348–357, 9 (5).
Atkinson, et al., J. Chem. Soc. C (1969), pp. 281–287, (2).
Chambers, et al., Tetrahedron (1969), pp. 565–572, 25 (3).
Segal, et al., J. Pharm. Sci. (1968), pp. 874–876, 57 (5).
Seikel, et al., Tetrahedron (1968), pp. 1475–1488, 24 (3).
Isaka, et al., Yakugaku Zasshi (1967), pp. 1288–1289, 87 (10).
Okuda, et al., Yakugaku Zasshi (1967), pp. 1003–1005, 87 (8).
Locksley, et al., Tetrahedron (1967), pp. 2229–2234, 23 (5).
Brown, Bull. Natl. Inst. Sci. India (1965), No. 31, pp. 167–178.
Chemical Abstracts, vol. 82, No. 15, Apr. 14, 1975 Columbus, Ohio; abstract No. 93567w, P.A. Hale et al: "Effects of epilation and hormones on the activity of rat hair follicles" p. 81; XP002141613 abstract & J. Exp. Zool., vol. 191, No. 1, 1975, pp. 49–62.
Chemical Abstracts, vol. 131, No. 17, Oct. 25, 1999 Columbus, Ohio, abstract No. 223774e Vinod. K. Sharma et al: "Evaluation of thyroid function in North Indians with alopecia areata: response to intravenous injection of 100microgram thyrotropin releasing hormone (TRH)", p. 125, XP002141564 abstract & J. Dermatol., vol. 26, No. 6, 1999, pp. 339–342.

METHOD OF TREATING HAIR LOSS USING DIPHENYLMETHANE DERIVATIVES

This application claims benefit of Ser. No. 60/137,024 filed Jun. 1, 1999.

FIELD OF THE INVENTION

The present invention relates to methods for treating hair loss in mammals, including arresting and/or reversing hair loss and promoting hair growth.

BACKGROUND OF THE INVENTION

Hair loss is a common problem which occurs, for example, through natural processes or is often chemically promoted through the use of certain therapeutic drugs designed to alleviate conditions such as cancer. Often such hair loss is accompanied by lack of hair regrowth which causes partial or full baldness.

As is well-known in the art, hair growth occurs by a cycle of activity which involves alternating periods of growth and rest. This cycle is often divided into three main stages which are known as anagen, catagen, and telogen. Anagen is the growth phase of the cycle and may be characterized by penetration of the hair follicle deep into the dermis with rapid proliferation of cells which are differentiating to form hair. The next phase is catagen, which is a transitional stage marked by the cessation of cell division, and during which the hair follicle regresses through the dermis and hair growth is ceased. The next phase, telogen, is often characterized as the resting stage during which the regressed follicle contains a germ with tightly packed dermal papilla cells. At telogen, the initiation of a new anagen phase is caused by rapid cell proliferation in the germ, expansion of the dermal papilla, and elaboration of basement membrane components. Wherein hair growth ceases, most of the hair follicles reside in telogen and anagen is not engaged, thus causing the onset of full or partial baldness.

There have been many attempts in the literature to invoke the regrowth of hair by, for example, the promotion or prolongation of anagen. Currently, there are two drugs approved by the United States Food and Drug Administration for the treatment of male pattern baldness: topical minoxidil (marketed as Rogaine® by Pharmacia & Upjohn), and oral finasteride (marketed as Propecia® by Merck & Co., Inc.). For several reasons, however, including safety concerns and/or lack of efficacy, the search for efficacious hair growth inducers is ongoing.

Interestingly, it is known that the thyroid hormone known as thyroxine ("T4") converts to thyronine ("T3") in human skin by deiodinase I, a selenoprotein. Selenium deficiency causes a decrease in T3 levels due to a decrease in deiodinase I activity; this reduction in T3 levels is strongly associated with hair loss. Consistent with this observation, hair growth is a reported side effect of administration of T4. See, e.g., Berman, "Peripheral Effects of L-Thyroxine on Hair Growth and Coloration in Cattle", *Journal of Endocrinology*, Vol. 20, pp. 282–292 (1960); and Gunaratnam, "The Effects of Thyroxine on Hair Growth in the Dog", *J. Small Anim. Pract.*, Vol. 27, pp. 17–29 (1986). Furthermore, T3 and T4 have been the subject of several patent publications relating to treatment of hair loss. See, e.g., Fischer et al., DE 1,617,477, published Jan. 8, 1970; Mortimer, GB 2,138,286, published Oct. 24, 1984; and Lindenbaum, WO 96/25943, assigned to Life Medical Sciences, Inc., published Aug. 29, 1996.

Unfortunately, however, administration of T3 and/or T4 to treat hair loss is not practicable because these thyroid hormones are also known to induce significant cardiotoxicity. See, e.g., Walker et al., U.S. Pat. No. 5,284,971, assigned to Syntex, issued Feb. 8, 1994 and Emmett et al., U.S. Pat. No. 5,061,798, assigned to Smith Kline & French Laboratories, issued Oct. 29, 1991. Surprisingly, however, the present inventors have discovered compounds which promote hair growth without inducing cardiotoxicity. Consistent with this discovery, but without intending to be limited by theory, the present inventors have surprisingly discovered that the compounds useful in the present invention interact strongly with hair-selective thyroid hormone receptors but interact less strongly, or not at all, with heart-selective hormone receptors. These unique properties are, of course, not shared with T3 and/or T4. Accordingly, the compounds described for use in the methods and compositions herein are cardiac-sparing compounds useful for treating hair loss, including arresting and/or reversing hair loss and promoting hair growth.

SUMMARY OF THE INVENTION

The present invention relates to methods for treating hair loss comprising administering a compound which has been found by the present inventors to be particularly useful for treating hair loss in mammals, including arresting and/or reversing hair loss and promoting hair growth. The compounds utilized in the present method have the structure:

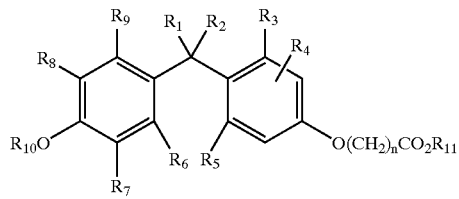

and pharmaceutically acceptable salts, hydrates, and biohydrolyzable amides, esters, and imides thereof, wherein $R_1$, $R_2$, $R_3$, $R_4$, $R_5$, $R_6$, $R_7$, $R_8$, $R_9$, $R_{10}$, $R_{11}$, and n are defined herein.

DETAILED DESCRIPTION OF THE INVENTION

The present invention relates to methods of using compounds and compositions which are particularly useful for treating hair loss in mammals, including arresting and/or reversing hair loss and promoting hair growth.

In addition to discovering that the present compounds are useful for treating hair loss, the present inventors have also surprisingly discovered that the preferred compounds are cardiac-sparing. The preferred compounds useful in the method of the present invention are therefore, as defined herein below, cardiac-sparing.

Publications and patents are referred to throughout this disclosure. All references cited herein are hereby incorporated by reference.

All percentages, ratios, and proportions used herein are by weight unless otherwise specified.

In the description of the invention various embodiments and/or individual features are disclosed. As will be apparent to the ordinarily skilled practitioner all combinations of such embodiments and features are possible and can result in preferred executions of the invention.

As used herein, wherein any variable, moiety, group, or the like occurs more than one time in any variable or structure, its definition at each occurrence is independent of its definition at every other occurrence.

Definition and Usage of Terms

The following is a list of definitions for terms used herein:

As used herein, "acyl" refers to the group —C(O)R, where R is lower alkyl or cycloalkyl, for example, acetyl, propionyl, cyclopropionyl, butanoyl, and the like.

As used herein, "alkoxy" is an oxygen radical having an alkyl substituent. Examples of alkoxy radicals include —O-methyl and —O-ethyl.

As used herein, "alkyl" is a saturated, straight or branched chain monovalent hydrocarbon radical. Unless otherwise specified, alkyls have from 1 to about 8 carbon atoms ($C_1$–$C_8$). Preferred alkyls include, for example, methyl, ethyl, propyl, iso-propyl, tert-butyl, n-butyl, sec-butyl, iso-butyl, n-hexyl, and n-octyl.

As used herein, "aryl" refers to a monovalent unsaturated aromatic carbocyclic radical having a single ring (e.g., phenyl) or two rings (e.g., naphthyl or biphenyl), which may optionally be mono-, di-, or tri-substituted, independently, with hydroxy, —COOH, lower alkyl, lower alkoxy, nitro, amino, alkylamino, dialkylamino, trifluoromethyl, and/or cyano.

As used herein, "biohydrolyzable amides" are amides of the compounds used in the present invention which do not interfere with the activity of the compound, or that are readily converted in vivo by a mammalian subject to yield an active compound.

As used herein, "biohydrolyzable esters" are esters of the compounds used in the present invention which do not interfere with the activity of the compound, or that are readily converted in vivo by a mammalian subject to yield an active compound.

As used herein, "biohydrolyzable imides" are imides of the compounds used in the present invention which do not interfere with the activity of the compound, or that are readily converted in vivo by a mammalian subject to yield an active compound.

As used herein, "cycloalkyl" is a monovalent monocyclic hydrocarbon radical having from three to eight carbon atoms, such as cyclopropyl, cyclobutyl, cyclopentyl, cyclohexyl, cycloheptyl, and cyclooctyl.

As used herein, "halogen" refers to chlorine, bromine, iodine, and fluorine, preferably chlorine, bromine, and iodine, more preferably chlorine and iodine, and most preferably iodine.

As used herein, "heteroaryl" refers to a monovalent aromatic carbocyclic radical having from 1 to 3 heteroatoms within a single ring, (e.g., pyridyl, imidazolyl, thiazolyl, pyrimidine, oxazolyl, and the like), which may optionally be mono-, di-, or tri-substituted, independently, with hydroxy, —COOH, lower alkyl, lower alkoxy, nitro, amino, alkylamino, dialkylamino, trifluoromethyl, and/or cyano.

As used herein, "lower alkoxy" means the group —O-(lower alkyl) wherein lower alkyl is as defined herein.

As used herein "lower alkyl" refers to an alkyl radical having from 1 to 6 carbon atoms ($C_1$–$C_6$), such as, for example, methyl, ethyl, propyl, iso-propyl, tert-butyl, butyl, n-hexyl, and the like, unless otherwise indicated.

As used herein, "pharmaceutically acceptable" means suitable for use in a human or other mammal.

As used herein, "safe and effective amount of a compound" (or composition, or the like) means an amount that is effective to exhibit biological activity, preferably wherein the biological activity is arresting and/or reversing hair loss or promoting hair growth, at the site(s) of activity in a mammalian subject, without undue adverse side effects (such as toxicity, irritation, or allergic response), commensurate with a reasonable benefit/risk ratio when used in the manner of this invention.

As used herein "salt" is a cationic salt formed at any acidic (e.g., carboxyl) group, or an anionic salt formed at any basic (e.g., amino) group. Many such salts are known in the art. Preferred cationic salts include the alkali metal salts (such as, for example, sodium and potassium), alkaline earth metal salts (such as, for example, magnesium and calcium), and organic salts. Preferred anionic salts include the halides (such as, for example, chloride salts). Such acceptable salts must, when administered, be appropriate for mammalian use.

Methods of the Present Invention

The present invention relates to methods of treating hair loss comprising administering a composition comprising a compound having the structure:

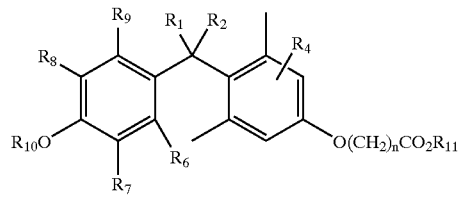

and pharmaceutically acceptable salts, hydrates, and biohydrolyzable amides, esters, and imides thereof, wherein:

(a) n is an integer from 1 to 3;

(b) $R_1$ and $R_2$ are each, independently, selected from hydrogen and lower alkyl; or wherein $R_1$ is hydrogen and $R_2$ is hydroxy; or wherein $R_1$ is doubly-bonded oxygen and $R_2$ is nil; or wherein $R_1$ is doubly-bonded sulfur and $R_2$ is nil;

(c) $R_4$ is selected from hydrogen, lower alkyl, and cycloalkyl;

(d) $R_6$ and $R_9$ are each, independently, selected from hydrogen and lower alkyl;

(e) $R_7$ and $R_8$ are each, independently, selected from hydrogen, lower alkyl, optionally substituted phenyl, optionally substituted benzyl, and heteroaryl; wherein at least one of $R_7$ and $R_8$ is not hydrogen;

(f) $R_{10}$ is selected from hydrogen, lower alkyl, cycloalkyl, and acyl;

(g) $R_{11}$ is selected from hydrogen, lower alkyl, and cycloalkyl.

The compounds useful in the method herein are further described in Scanlan et al., WO 98/57919, assigned to The Regents of the University of California, published Dec. 23, 1998 and Scanlan et al., U.S. Pat. No. 5,883,294, The Regents of the University of California, issued Mar. 16, 1999. However, for convenience, the compounds are more fully described herein below:

The compounds useful in the present invention are dimethyl-substituted biphenyl compounds linked through a carbon atom linker, wherein the linker is optionally substituted with $R_1$ and/or $R_2$. Each of the phenyl rings of the biphenyl compound are substituted with at least one moiety, as is described below.

The $R_1$ and $R_2$ Moieties $R_1$ and $R_2$ substituted on the carbon linker and are each, independently, selected from hydrogen and lower alkyl.

Alternatively, $R_1$ is hydrogen and $R_2$ is hydroxy; or $R_1$ is doubly-bonded oxygen (=O) and $R_2$ is nil; or $R_1$ is doubly-bonded sulfur (=S) and $R_2$ is nil. Preferably, $R_1$ is selected from methyl, hydrogen, and doubly-bonded oxygen. Preferably, $R_2$ is selected from methyl and hydrogen. More preferably, at least one of $R_1$ and $R_2$ is hydrogen. Most preferably, $R_1$ and $R_2$ are each hydrogen.

The $R_4$ Moiety $R_4$ may substitute at any available position on the designated phenyl ring. $R_4$ is selected from hydrogen, lower alkyl, and cycloalkyl. Preferably, $R_4$ is hydrogen.

The $R_6$ and $R_9$ Moieties $R_6$ and $R_9$ are each, independently, selected from hydrogen and lower alkyl. Preferably, $R_6$ and $R_9$ are each, independently, selected from hydrogen and n-butyl. More preferably, at least one of $R_6$ and $R_9$ is hydrogen. Most preferably $R_6$ and $R_9$ are each hydrogen.

The $R_7$ and $R_8$ Moieties $R_7$ and $R_8$ are each, independently, selected from hydrogen, lower alkyl, optionally substituted phenyl, optionally substituted benzyl, and heteroaryl; wherein at least one of $R_7$ and $R_8$ is not hydrogen. Preferably $R_7$ and $R_8$ are each, independently, selected from hydrogen and iso-propyl. More preferably, $R_7$ is hydrogen and $R_8$ is iso-propyl.

The $R_{10}$ Moiety

The $R_{10}$ moiety substitutes on the indicated oxygen atom. $R_{10}$ is selected from hydrogen, lower alkyl, cycloalkyl, and acyl. Preferably $R_{10}$ is selected from hydrogen and lower alkyl, preferably hydrogen and methyl. Most preferably, $R_{10}$ is hydrogen.

The Integer n

The integer n determines the number of methylene groups in the respective moiety. The integer n is from 1 to 3, and is most preferably 1.

The $R_{11}$ Moiety

The $R_{11}$ moiety is selected from hydrogen, lower alkyl, and cycloalkyl. Preferably, $R_{11}$ is selected from hydrogen and lower alkyl. Most preferably, $R_{11}$ is hydrogen.

Analytical Methods

The present invention relates to methods of treating hair loss by administering a compound having a structure as described herein. Preferably, the compound utilized in the present invention will be cardiac-sparing. Compounds (test compounds) may be tested for their ability to induce anagen and their lack of cardiotoxicity (cardiac-sparing) using the following methods. Alternatively, other methods well-known in the art may be used (but with the term "cardiac-sparing" being defined according to the method disclosed herein below).

Cardiotoxicity Assay:

The cardiotoxicity assay measures the potential of a test compound to adversely affect the cardiovascular system. As thyroid hormone (T3) damages the cardiovascular system, the heart enlarges. See, e.g., Gomberg-Maitland et al., "Thyroid hormone and Cardiovascular Disease", *American Heart Journal*, Vol. 135(2), pp. 187–196 (1998); Klein and Ojamaa, "Thyroid Hormone and the Cardiovascular System", *Current Opinion in Endocrinology and Diabetes*, Vol. 4, pp.341–346 (1997); and Klemperer et al., "Thyroid Hormone Therapy and Cardiovascular Disease", *Progress in Cardiovascular Diseases*, Vol. 37 (4), pp. 329–336 (1996). This increases the weight of the heart relative to whole body weight. The cardiotoxicity assay herein below is used to test compounds for potentially adverse cardiac effects by measuring their effect on the heart-to-body weight ratio.

Two groups each of six male Sprague Dawley rats (Harlan Sprague Dawley, Inc., Indianapolis, Ind.) (each weighing from approximately 220 grams to 235 grams) are utilized. The first group is a vehicle control group and the second group is a test compound group. The length of the assay is 30 days, with treatment of vehicle or test compound in vehicle daily for 28 of those days as described below.

Prior to initiation of the assay, each rat is allowed to acclimate to standard environmental conditions for 5 days. Each rat receives food (standard rat chow diet) and water ad libitum 5 days prior to initiation of the assay as well as to termination of the study.

The vehicle is 91:9 (v:v) propylene glycol:ethanol. The test compound is prepared at a concentration of 500 $\mu$g/mL in the vehicle.

Each rat is weighed on day 1 of the assay. Dosage calculations are then performed: each rat will be administered daily a dosing solution of vehicle or test compound in vehicle (depending on whether the rat is in the vehicle control group or the test compound group, respectively) at 500 $\mu$L of dosing solution per kg of rat. For rats in the test compound group, this corresponds to a dose of 250 $\mu$g of test compound per kg of rat.

Day 2 is the first day of treatment with dosing solution for both groups. Body weights are taken for each rat on days 3, 5, 8, 10, 12, 15, 17, 19, 22, 24, 26, and 29 prior to dosing for that day; for each rat, the dosing solutions are recalculated and administered accordingly upon change in body weight.

Treatment occurs once daily in the morning on days 2 through 29, inclusive, for each rat in each group. For each treatment, the dosing solution is administered subcutaneously between the shoulders of the rat such that the injection sites are rotated in this area.

On day 30 in the morning, the rats of each group are euthanized with $CO_2$ from dry ice. Each rat is immediately weighed for total body weight.

The hearts of each rat are then excised as follows. An incision is made to expose the abdominal cavity. The rib cage is carefully cut at the sternum with small scissors, such that the heart and lungs are exposed. With small scissors and forceps, the vessels connected to the heart are cut away from the heart. These vessels include the caudal vena cava, left cranial vena cava (pulmonary trunk), right cranial vena cava, thoracic aorta, right subclavian artery, internal thoracic artery and vein, and any other small attachments. The heart is then immediately taken out intact, including the left and right auricles and left and right ventricles. Immediately thereafter, any excess tissue is trimmed away, the heart is lightly blotted on a paper towel until no more blood is visibly left behind on the paper towel, and the heart is weighed.

The heart weight is divided by the body weight after euthanization for each rat to give the heart/body ratio. The heart/body ratios for each rat in the vehicle control group are added together and divided by 6 (i.e., the total number of rats in the group) to give RV (ratio for vehicle control group). Similarly, the heart/body ratios for each rat in the test compound group are added together and divided by 6 to give RT (ratio for test compound group).

The index C is then calculated by dividing RT by RV. As defined herein, where C is less than 1.3, the test compound is cardiac-sparing. Preferably, C is less than 1.2, more preferably less than 1.15, and most preferably less than 1.1. In accordance with this method, T3 and T4 are not cardiac-sparing.

Telogen Conversion Assay:

The Telogen Conversion Assay measures the potential of a test compound to convert mice in the resting stage of the hair growth cycle ("telogen"), to the growth stage of the hair growth cycle ("anagen").

Without intending to be limited by theory, there are three principal phases of the hair growth cycle: anagen, catagen, and telogen. It is believed that there is a longer telogen period in C3H mice (Harlan Sprague Dawley, Inc., Indianapolis, Ind.) from approximately 40 days of age until about 75 days of age, when hair growth is synchronized. It is believed that after 75 days of age, hair growth is no longer synchronized. Wherein about 40 day-old mice with dark fur (brown or black) are used in hair growth experiments, melanogenesis occurs along with hair (fur) growth wherein the topical application of hair growth inducers are evaluated. The Telogen Conversion Assay herein below is used to screen compounds for potential hair growth by measuring melanogenesis.

Three groups of 44 day-old C3H mice are utilized: a vehicle control group, a positive control group, and a test compound group, wherein the test compound group is administered a compound used in the method of the present invention. The length of the assay is at least 19 days with 15 treatment days (wherein the treatment days occur Mondays through Fridays). Day 1 is the first day of treatment. Most studies will end on Day 19, but a few may be carried out to Day 24 if the melanogenesis response looks positive, but occurs slowly. A typical study design is shown in Table 1 below. Typical dosage concentrations are set forth in Table 1, however the skilled artisan will readily understand that such concentrations may be modified.

TABLE 1

| Group # | Animal # | Compound | Concentration | Application volume | Length of Study |
|---|---|---|---|---|---|
| 1 | 1–10 | Test Compound | 0.1% in vehicle** | 400 µL topical | 19 or 24 days |
| 2 | 11–20 | Positive Control (T3) | 0.01% in vehicle** | 400 µL topical | 19 or 24 days |
| 3 | 21–30 | Vehicle** | N/A | 400 µL topical | 19 or 24 days |

**The vehicle is 60% ethanol, 20% propylene glycol, and 20% dimethyl isosorbide (commercially available from Sigma Chemical Co., St. Louis, MO).

The mice are treated topically Monday through Friday on their lower back (base of tail to the lower rib). A pipettor and tip are used to deliver 400 µL to each mouse's back. The 400 µL application is applied slowly while moving hair on the mouse to allow the application to reach the skin.

While each treatment is being applied to the mouse topically, a visual grade of from 0 to 4 will be given to the skin color in the application area of each animal. As a mouse converts from telogen to anagen, its skin color will become more bluish-black. As indicated in Table 2, the grades 0 to 4 represent the following visual observations as the skin progresses from white to bluish-black.

TABLE 2

| Visual Observation | Grade |
|---|---|
| Whitish Skin Color | 0 |
| Skin is light gray (indication of initiation of anagen) | 1 |
| Appearance of Blue Spots | 2 |
| Blue Spots are aggregating to form one large blue area | 3 |
| Skin is dark blue (almost black) with color covering majority of treatment area (indication of mouse in full anagen) | 4 |

Method of Making

The compounds used in the methods of the present invention are prepared according to procedures which are well-known to those ordinarily skilled in the art. The starting materials used in preparing the compounds are known, made by known methods, or are commercially available as a starting material.

It is recognized that the ordinarily skilled artisan in the art of organic chemistry can readily carry out standard manipulations of organic compounds without further direction. Examples of such manipulations are discussed in standard texts such as J. March, *Advanced Organic Chemistry*, John Wiley & Sons (1992).

The ordinarily skilled artisan will readily appreciate that certain reactions are best carried out when other functionalities are masked or protected in the compound, thus increasing the yield of the reaction and/or avoiding any undesirable side reactions. Often, the artisan utilizes protecting groups to accomplish such increased yields or to avoid the undesired reactions. These reactions are found in the literature and arc also well within the scope of the skilled artisan. Examples of many such manipulations can be found in, for example, T. Greene, *Protecting Groups in Organic Synthesis*, John Wiley & Sons (1981).

The compounds of the present invention may have one or more chiral centers. As a result, one may selectively prepare one optical isomer, including diastereomers and enantiomers, over another, for example by chiral starting materials, catalysts or solvents, or may prepare both stereoisomers or both optical isomers, including diastereomers and enantiomers at once (a racemic mixture). Since the compounds of the invention may exist as racemic mixtures, mixtures of optical isomers, including diastereomers and enantiomers, may be separated using known methods, such as through the use of, for example, chiral salts and chiral chromatography.

In addition, it is recognized that one optical isomer, including a diastereomer and enantiomer, or a stereoisomer, may have favorable properties over the other. Thus, when disclosing and claiming the invention, when one racemic mixture is disclosed, it is clearly contemplated that both optical isomers, including diastereomers and enantiomers, or stereoisomers substantially free of the other are disclosed and claimed as well.

The syntheses of the compounds useful in the present invention are described in the art. Accordingly, the ordinarily skilled artisan will be able to prepare the compounds described herein. For further guidance, the syntheses of the present compounds are described in Scanlan et al., WO 98/57919, assigned to The Regents of the University of California, published Dec. 23, 1998 and Scanlan et al., U.S. Pat. No. 5,883,294, assigned to The Regents of the University of California, issued Mar. 16, 1999. For convenience, non-limiting syntheses of the compounds used herein are set forth in the examples below.

EXAMPLE 1

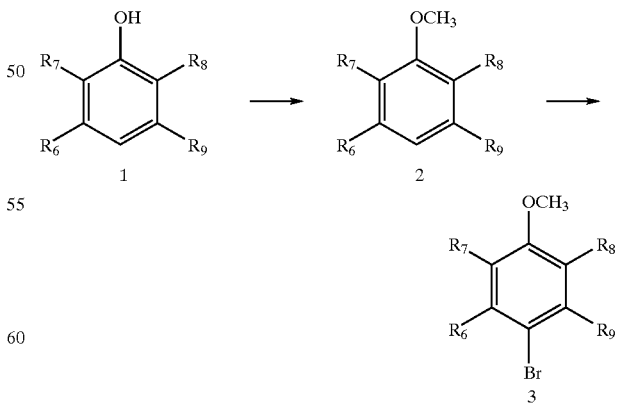

Compounds of Formula 1 are commercially available, or are prepared by means well known in the art. Generally, the phenol of Formula 1 is protected by conversion to, for example, the methoxy derivative, for example by reacting 1 with methyl iodide in the presence of a base such as, for example, potassium carbonate, in a polar solvent such as N,N-dimethylformamide (DMF). When the reaction is substantially complete, the protected phenol 2 is isolated and purified by conventional means, such as flash chromatography. In protecting the phenol, other protecting groups may be utilized instead of methoxy such as, for example, a silyl protecting group (e.g., tert-butyldimethylsilyloxy).

The compound of Formula 2 may be brominated using potassium bromide in the presence of a crown ether such as, for example, 18-Crown-6, and an oxidizing agent such as, for example, 3-chloroperoxy benzoic acid. The reaction is carried out in an inert solvent such as, for example, dichloromethane. When the reaction is substantially complete, the 4-bromo derivative of Formula 3 is isolated and purified by conventional means such as, for example, flash chromatography.

EXAMPLE 2

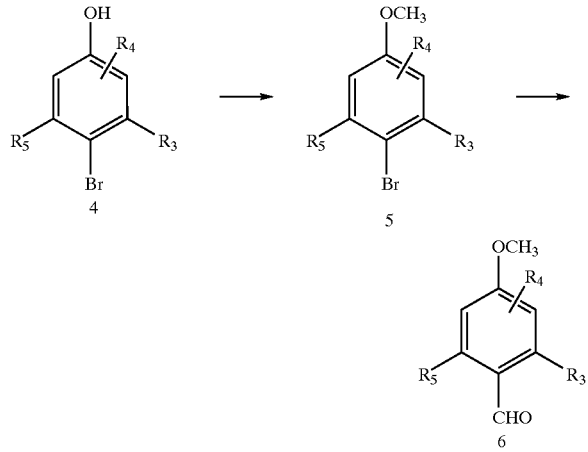

Compounds having Formula 4 are commercially available, or may be prepared by means well known to one ordinarily skilled in the art. In general, the phenol of Formula 4 is protected by conversion to the methoxy derivative, or other conventional phenol protecting groups, as disclosed in Example 1 herein above, to give a p-bromo compound of Formula 5.

The bromo moiety of 5 is then converted to a formyl group. The reaction is carried out conventionally, adding t-butyllithium to a solution of 5 in an inert solvent at about −78° C., preferably tetrahydrofuran (THF), and adding DMF to the cold solution. After stirring, the mixture is allowed to warm to room temperature. The 4-formyl derivative of Formula 6 is isolated and purified by conventional means, preferably by flash chromatography.

EXAMPLE 3

The compounds utilized in the present invention are prepared as shown below.

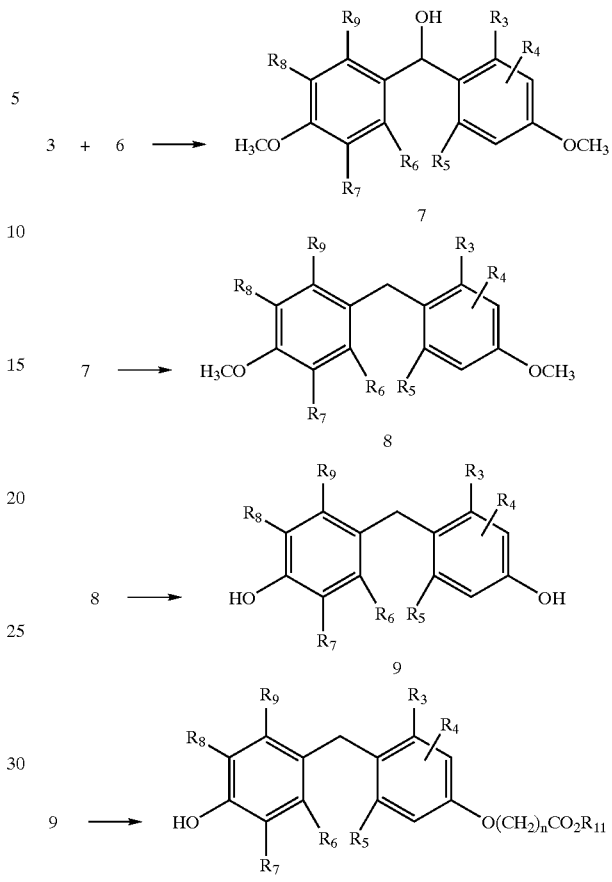

Compounds of Formula 7 are prepared by reaction of compounds 3 and 6. Generally, the p-bromo compound 3 is dissolved in an inert solvent, preferably tetrahydrofuran, cooled to about −78° C., and tert-butyllithium is added. The mixture is stirred for about 10 minutes and compound 6 is added. After stirring, the mixture is allowed to warm to room temperature. When the reaction is substantially complete, the compound of Formula 7 is isolated and purified by conventional means, preferably by flash chromatography.

The compound of Formula 7 is then hydrogenated to remove the hydroxy group. Generally, a platinum or palladium catalyst is used, preferably palladium on carbon. The reaction is carried out in an acidic medium, preferably acetic acid in ethanol, under an atmosphere of hydrogen and room temperature and pressure. The compound of Formula 8 is isolated by conventional means, and preferably used with no further purification.

The compound of Formula 8 is then demethylated. The reaction is carried out conventionally, using boron tribromide in dichloromethane. The compound of Formula 9 is isolated and purified by conventional means, preferably by flash chromatography.

The compound of Formula 9 is converted to I wherein $R_{10}$ is hydrogen by reaction with a halo ester of formula X—$(CH_2)nCO_2R_{11}$, wherein X is chloro, bromo, or iodo, n is 1, 2, or 3, and $R_{11}$ is lower alkyl, for example, tert-butyl. The compound 9 is dissolved in an inert solvent, for example tetrahydrofuran, cooled to about −25° C., and cesium carbonate is added followed by the halo ester. The mixture is stirred for about 1 hour, then allowed to warm to room temperature. The ester of compound I is isolated and purified by conventional means, preferably by flash chromatography. The ester is then dissolved in a protic solvent, preferably methanol, and hydrolyzed with a base, preferably sodium hydroxide. Upon acidification, the compound I is isolated and purified by conventional means.

EXAMPLE 4

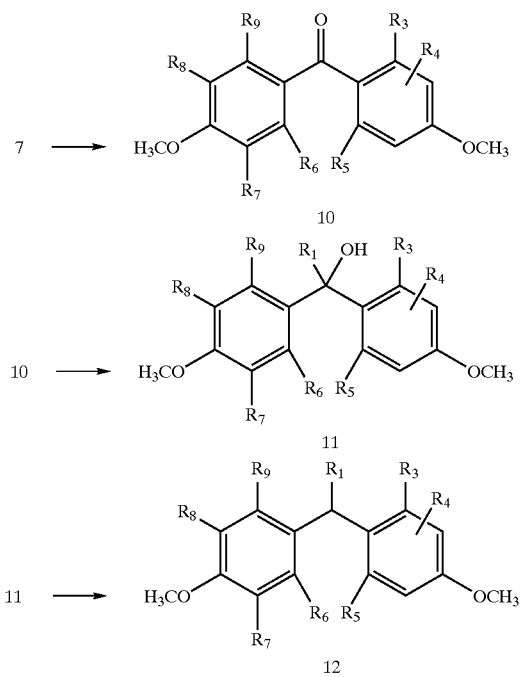

EXAMPLE 5

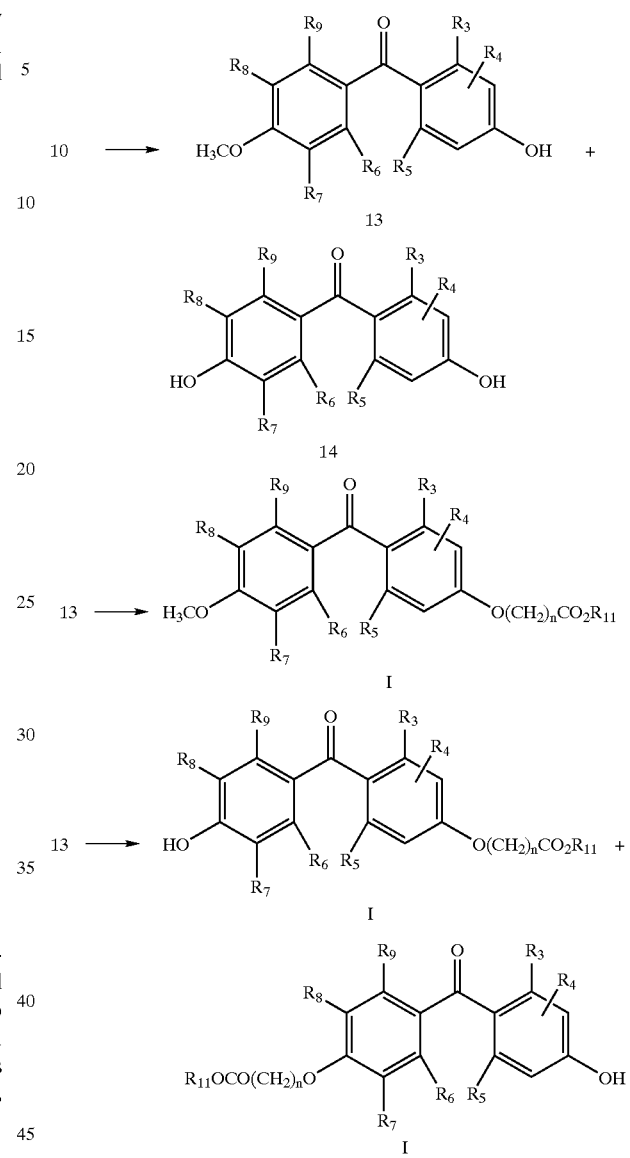

The ketones of Formula 10 are prepared from the compounds of Formula 7 by oxidation. Generally, 7 is dissolved in an inert solvent, preferably dichloromethane, cooled to about 0° C., and an oxidizing agent such as pyridinium dichromate is added. The mixture is stirred about 4 hours and then 11 is isolated and purified by conventional means, preferably by flash chromatography.

The compound 10 is then reacted with an organo cerium complex to give 11. In general, anhydrous cerium chloride is stirred in an inert solvent, preferably tetrahydrofuran, at room temperature for about 2 hours in an inert atmosphere. The resultant suspension is cooled to about −78° C. and an organolithium complex of formula $R_1Li$ is added. Stirring continues for about thirty minutes, after which time the compound 10 is added in an inert solvent, preferably tetrahydrofuran. The mixture is stirred about three hours at −78° C., and then warmed to about 0° C. The compound 11 is isolated by conventional means, preferably through column chromatography.

The compound 11 is then hydrogenated to the compound 12 in the same manner as shown for the conversion of 7 to 8 above.

The compound 12 is then treated with boron tribromide as shown above for the conversion of 8 to 9 above to give a 4,4'-dihydroxy derivative, which is converted to a compound of Formula I as shown above for the conversion of 9 to a compound of Formula I wherein $R_{10}$ is hydrogen, by reaction with an ester of formula $X(CH_2)_nCO_2R_{11}$.

The ketone 10, prepared as shown above, is treated with boron tribromide in the same manner as shown above for the conversion of 8 to 9. A mixture of compounds is obtained, a 4,4'-dihydroxy compound 14, and a 4-hydroxy4'-methoxy derivative 13.

The 4-hydroxy4'-derivative 13 is then converted to a compound of Formula I wherein $R_{10}$ is methyl by reaction with an ester of formula $X(CH_2)_nCO_2R$, in the same manner as shown above for the conversion of 9 to a compound of Formula I. The 4,4'-dihydroxy compound 14, when subjected to the same conditions, gives a mixture of two compounds a 4'-hydroxy4-oxyalkanoic acid of Formula I and a 4-hydroxy4'-oxyalkanoic acid of Formula I.

EXAMPLE 6

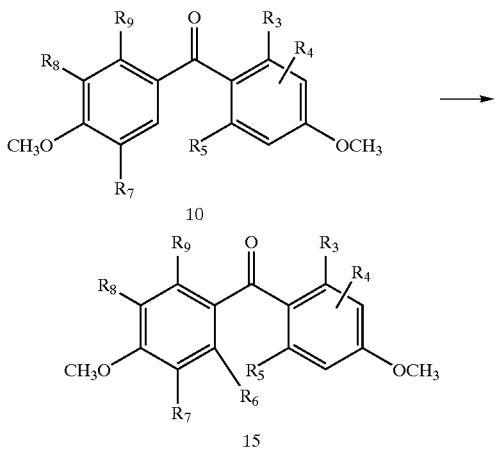

A compound for use in the present invention is prepared wherein $R_6$ is lower alkyl. Anhydrous cerium chloride is reacted with an alkyl lithium, for example n-butyllithium, at about room temperature in an inert solvent such as tetrahydrofuran, to obtain a lithium cerium complex. The suspension obtained is cooled to about −78° C., and the ketone 10 (prepared as described above) is added. The reaction stirs about 3 hours at this temperature, followed by stirring about 2 hours at 0° C. The compound 15 is isolated by conventional means and is preferably purified by flash chromatography.

The compound 15 is treated with boron tribromide in the same manner as shown above for the conversion of 8 to 9, to yield a 4,4'-dihydroxy compound, which is converted to a compound of Formula I wherein $R_6$ is lower alkyl by reaction with an ester of formula $X(CH_2)_nCO_2R$, in the same manner as shown above for the conversion of 9 to a compound of Formula I, to give a mixture of three compounds: a 4'-hydroxy-4-oxyalkanoic acid of Formula I, a 4-hydroxy-4'-oxyalkanoic acid of Formula I, and a 4,4'-bis (oxyalkanoic acid) of Formula I.

Use of the Present Compounds

The methods of the present invention are performed by administering to a mammal (preferably a human) a compound having a structure as described herein and, preferably, a pharmaceutically-acceptable or cosmetically-acceptable carrier.

The compounds herein may be used for the treatment of such conditions as treating hair loss in mammals, including arresting and/or reversing hair loss and promoting hair growth. Such conditions may manifest themselves in, for example, alopecia, including male pattern baldness and female pattern baldness.

Preferably the compounds of the present invention are, as defined herein, cardiac-sparing.

Preferably, in the methods of the present invention, the compounds are formulated into pharmaceutical or cosmetic compositions for use in treatment or prophylaxis of conditions such as the foregoing. Standard pharmaceutical formulation techniques are used, such as those disclosed in *Remington's Pharmaceutical Sciences*, Mack Publishing Company, Easton, Pa. (1990).

Typically, from about 5 mg to about 3000 mg, more preferably from about 5 mg to about 1000 mg, more preferably from about 10 mg to about 100 mg, of a compound having a structure as described herein is administered per day for systemic administration. It is understood that these dosage ranges are by way of example only, and that daily administration can be adjusted depending on various factors. The specific dosage of the compound to be administered, as well as the duration of treatment, and whether the treatment is topical or systemic are interdependent. The dosage and treatment regimen will also depend upon such factors as the specific compound used, the treatment indication, the efficacy of the compound, the personal attributes of the subject (such as, for example, weight, age, sex, and medical condition of the subject), compliance with the treatment regimen, and the presence and severity of any side effects of the treatment.

According to the present invention, the subject compounds are co-administered with a pharmaceutically-acceptable or cosmetically-acceptable carrier (herein collectively described as "carrier"). The term "carrier", as used herein, means one or more compatible solid or liquid filler diluents or encapsulating substances which are suitable for administration to a mammal. The term "compatible", as used herein, means that the components of the composition are capable of being commingled with a compound of the present invention, and with each other, in a manner such that there is no interaction which would substantially reduce the efficacy of the composition under ordinary use situations. Carriers must, of course, be of sufficiently high purity and sufficiently low toxicity to render them suitable for administration to the animal, preferably mammal (most preferably human), being treated. The carrier can itself be inert or it can possess pharmaceutical and/or cosmetic benefits of its own.

The compositions of this invention may be in any of a variety of forms, suitable (for example) for oral, rectal, topical, nasal, ocular or parenteral administration. Of these, topical and/or oral administration are especially preferred with topical being most preferred. Depending upon the particular route of administration desired, a variety of carriers well-known in the art may be used. These include solid or liquid fillers, diluents, hydrotropes, surface-active agents, and encapsulating substances. Optional pharmaceutically-active or cosmetically-active materials may be included which do not substantially interfere with the activity of the compound of the present invention. The amount of carrier employed in conjunction with the compound is sufficient to provide a practical quantity of material for administration per unit dose of the compound. Techniques and compositions for making dosage forms useful in the methods of this invention are described in the following references: *Modern Pharmaceutics*, Chapters 9 and 10, Banker & Rhodes, eds. (1979); Lieberman et al., *Pharmaceutical Dosage Forms: Tablets* (1981); and Ansel, *Introduction to Pharmaceutical Dosage Forms*, $2^{nd}$ Ed., (1976).

Some examples of substances which can serve as carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the TWEENS; wetting agents, such sodium lauryl sulfate; coloring agents; flavoring agents; tableting agents, stabilizers; antioxidants; preservatives; pyrogen-free water; isotonic saline; and phosphate buffer solutions.

The choice of a carrier to be used in conjunction with the subject compound is typically determined by the way the compound is to be administered.

In particular, carriers for systemic administration include sugars, starches, cellulose and its derivatives, malt, gelatin, talc, calcium sulfate, vegetable oils, synthetic oils, polyols, alginic acid, phosphate buffer solutions, emulsifiers, isotonic saline, and pyrogen-free water. Preferred carriers for parenteral administration include propylene glycol, ethyl oleate, pyrrolidone, ethanol, and sesame oil. Preferably, the carrier, in compositions for parenteral administration, comprises at least about 90% by weight of the total composition.

Various oral dosage forms can be used, including such solid forms as tablets, capsules, granules and bulk powders. These oral forms comprise a safe and effective amount, usually at least about 5%, and preferably from about 25% to about 50%, of a compound used in the present invention. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

The carriers suitable for the preparation of unit dosage forms for oral administration are well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules (including time release and sustained release formulations) typically comprise one or more solid diluents disclosed above. The selection of carrier components depends on secondary considerations like taste, cost, and shelf stability, which are not critical for the purposes of the subject invention, and can be readily made by a person skilled in the art.

Orally administered compositions also include liquid solutions, emulsions, suspensions, powders, granules, elixirs, tinctures, syrups, and the like. The carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, AVICEL RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit coatings, waxes and shellac.

Other compositions useful for attaining systemic delivery of the subject compounds include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

The compounds of the present invention may also be topically administered. The carrier of the topical composition preferably aids penetration of the present compounds into the skin to reach the environment of the hair follicle. Topical compositions of the present invention may be in any form including, for example, solutions, oils, creams, ointments, gels, lotions, shampoos, leave-on and rinse-out hair conditioners, milks, cleansers, moisturizers, sprays, skin patches, and the like.

Topical compositions containing the active compound can be admixed with a variety of carrier materials well known in the art, such as, for example, water, alcohols, aloe vera gel, allantoin, glycerine, vitamin A and E oils, mineral oil, propylene glycol, PPG-2 myristyl propionate, and the like.

Other materials suitable for use in topical carriers include, for example, emollients, solvents, humectants, thickeners and powders. Examples of each of these types of materials, which can be used singly or as mixtures of one or more materials, are as follows:

Emollients, such as stearyl alcohol, glyceryl monoricinoleate, glyceryl monostearate, propane-1,2-diol, butane-1,3-diol, mink oil, cetyl alcohol, iso-propyl isostearate, stearic acid, iso-butyl palmitate, isocetyl stearate, oleyl alcohol, isopropyl laurate, hexyl laurate, decyl oleate, octadecan-2-ol, isocetyl alcohol, cetyl palmitate, dimethylpolysiloxane, di-n-butyl sebacate, iso-propyl myristate, iso-propyl palmitate, iso-propyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, and myristyl myristate; propellants, such as propane, butane, iso-butane, dimethyl ether, carbon dioxide, and nitrous oxide; solvents, such as ethyl alcohol, methylene chloride, iso-propanol, castor oil, ethylene glycol monoethyl ether, diethylene glycol monobutyl ether, diethylene glycol monoethyl ether, dimethyl sulphoxide, dimethyl formamide, tetrahydrofuran; humectants, such as glycerin, sorbitol, sodium 2-pyrrolidone-5-carboxylate, soluble collagen, dibutyl phthalate, and gelatin; and powders, such as chalk, talc, fullers earth, kaolin, starch, gums, colloidal silicon dioxide, sodium polyacrylate, tetra alkyl ammonium smectites, trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, and ethylene glycol monostearate.

The compounds used in the present invention may also be administered in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholines. A preferred formulation for topical delivery of the present compounds utilizes liposomes such as described in Dowton et al., "Influence of Liposomal Composition on Topical Delivery of Encapsulated Cyclosporin A: I. An in vitro Study Using Hairless Mouse Skin", *S. T. P. Pharma Sciences*, Vol. 3, pp. 404–407 (1993); Wallach and Philippot, "New Type of Lipid Vesicle: Novasome®", *Liposome Technology*, Vol. 1, pp. 141–156 (1993); Wallach, U.S. Pat. No. 4,911,928, assigned to Micro-Pak, Inc., issued Mar. 27, 1990; and Weiner et al., U.S. Pat. No. 5,834,014, assigned to The University of Michigan and Micro-Pak, Inc., issued Nov. 10, 1998 (with respect to Weiner et al., with a compound as described herein administered in lieu of, or in addition to, minoxidil).

The compounds of the present invention may also be administered by iontophoresis. See, e.g., internet site www.unipr.it/arpa/dipfarm/erasmus/erasm14.html; Banga et al., "Hydrogel-based Iontotherapeutic Delivery Devices for Transdermal Delivery of Peptide/Protein Drugs", *Pharm. Res.*, Vol. 10 (5), pp. 697–702 (1993); Ferry, "Theoretical Model of Iontophoresis Utilized in Transdermal Drug Delivery", *Pharmaceutical Acta Helvetiae*, Vol 70, pp. 279–287 (1995); Gangarosa et al., "Modern Iontophoresis for Local Drug Delivery", *Int. J. Pharm*, Vol. 123, pp. 159–171 (1995); Green et al., "Iontophoretic Delivery of a Series of Tripeptides Across the Skin in vitro", *Pharm. Res.*, Vol 8, pp. 1121–1127 (1991); Jadoul et al., "Quantification and Localization of Fentanyl and TRH Delivered by Iontophoresis in the Skin", *Int. J. Pharm.*, Vol. 120, pp. 221–8 (1995); O'Brien et al., "An Updated Review of its Antiviral Activity, Pharmacokinetic Properties and Therapeutic Efficacy", *Drugs*, Vol. 37, pp. 233–309 (1989); Parry et al., "Acyclovir Biovailability in Human Skin", *J. Invest. Dermatol.*, Vol. 98 (6), pp. 856–63 (1992); Santi et al., "Drug Reservoir Composition and Transport of Salmon Calcitonin in Transdermal Iontophoresis", *Pharm. Res.*, Vol 14 (1), pp. 63–66 (1997); Santi et al., "Reverse Iontophoresis—Parameters Determining Electroosmotic Flow: I. pH and Ionic Strength", *J. Control. Release*, Vol. 38, pp. 159–165 (1996); Santi et al., "Reverse Iontophoresis—Parameters Determining Electroosmotic Flow: II. Electrode Chamber Formulation", *J. Control. Release*, Vol. 42, pp. 29–36 (1996); Rao et al., "Reverse Iontophoresis: Noninvasive Glucose Monitoring in vivo in Humans", *Pharm. Res.*, Vol. 12 (12), pp. 1869–1873 (1995); Thysman et al., "Human Calcitonin Delivery in Rats by Iontophoresis", *J Pharm. Pharmacol.*, Vol. 46, pp. 725–730 (1994); and Volpato et al., "Iontophoresis Enhances the Transport of Acyclovir through Nude Mouse Skin by Electrorepulsion and Electroosmosis", *Pharm. Res.*, Vol. 12 (11), pp. 1623–1627 (1995).

The compositions used in the present invention may also optionally comprise an activity enhancer. The activity enhancer can be chosen from a wide variety of molecules which can function in different ways to enhance hair growth effects of a compound of the present invention. Particular classes of activity enhancers include other hair growth stimulants and penetration enhancers.

Non-limiting examples of other hair growth stimulants which may be used in the compositions herein, including both systemic and topical compositions, include, for example, benzalkonium chloride, benzethonium chloride, phenol, estradiol, diphenhydramine hydrochloride, chlorpheniramine maleate, chlorophyllin derivatives, cholesterol, salicylic acid, cysteine, methionine, red pepper tincture, benzyl nicotinate, D,L—menthol, peppermint oil, calcium pantothenate, panthenol, castor oil, hinokitiol, prednisolone, resorcinol, monosaccharides and esterified monosaccharides, chemical activators of protein kinase C enzymes, glycosaminoglycan chain cellular uptake inhibitors, inhibitors of glycosidase activity, glycosaminoglycanase inhibitors, esters of pyroglutamic acid, hexosaccharic acids or acylated hexosaccharic acids, aryl-substituted ethylenes, N-acylated amino acids, and, of course, minoxidil or finasteride. The most preferred activity enhancers are minoxidil and finasteride, most preferably minoxidil.

Non-limiting examples of penetration enhancers which may be used in the compositions herein include, for example, 2-methyl propan-2-ol, propan-2-ol, ethyl-2-hydroxypropanoate, hexan-2,5-diol, POE(2) ethyl ether, di(2-hydroxypropyl) ether, pentan-2,4-diol, acetone, POE(2) methyl ether, 2-hydroxypropionic acid, 2-hydroxyoctanoic acid, propan-1-ol, 1,4-dioxane, tetrahydrofuran, butan-1,4-diol, propylene glycol dipelargonate, polyoxypropylene 15 stearyl ether, octyl alcohol, POE ester of oleyl alcohol, oleyl alcohol, lauryl alcohol, dioctyl adipate, dicapryl adipate, di-isopropyl adipate, di-isopropyl sebacate, dibutyl sebacate. diethyl sebacate, dimethyl sebacate, dioctyl sebacate, dibutyl suberate, dioctyl azelate, dibenzyl sebacate, dibutyl phthalate, dibutyl azelate, ethyl myristate, dimethyl azelate, butyl myristate, dibutyl succinate, didecyl phthalate, decyl oleate, ethyl caproate, ethyl salicylate, iso-propyl palmitate, ethyl laurate, 2-ethyl-hexyl pelargonate, iso-propyl isostearate, butyl laurate, benzyl benzoate, butyl benzoate, hexyl laurate, ethyl caprate, ethyl caprylate, butyl stearate, benzyl salicylate, 2-hydroxypropanoic acid, 2-hyroxyoctanoic acid, dimethyl sulphoxide, N,N-dimethyl acetarnide, N,N-dimethyl formamide, 2-pyrrolidone, 1-methyl-2-pyrrolidone, 5-methyl-2-pyrrolidone, 1,5-dimethyl-2-pyrrolidone, 1-ethyl-2-pyrrolidone, phosphine oxides, sugar esters, tetrahydrofurfural alcohol, urea, diethyl-m-toluamide, and, 1-dodecylazacyloheptan-2-one.

In all of the foregoing, of course, the compounds used in the present methods can be administered alone or as mixtures, and the compositions may further include additional drugs or excipients as appropriate for the indication.

The present invention further relates to kits comprising a compound and/or composition herein and information and/or instructions by words, pictures, and/or the like, that use of the kit will provide treatment for hair loss in mammals (particularly humans) including, for example, arresting and/or reversing hair loss and/or promoting hair growth. In addition or in the alternative, the kit may comprise a compound and/or composition herein and information and/or instructions regarding methods of application of the compound and/or composition, preferably with the benefit of treating hair loss in mammals.

EXAMPLES OF COMPOSITION ADMINISTRATION

The following examples do not limit the invention, but provide guidance to the skilled artisan to perform the methods of the present invention. In each example, a compound other than the one mentioned may be substituted in the example by another having a structure as described herein with similar results.

EXAMPLE A

A composition for topical administration is made, comprising:

| Component | Amount |
|---|---|
| (3,5-dimethyl-4-(4'-hydroxy-3'-isopropylbenzyl)phenoxy)acetic acid | 5% |
| Ethanol | 57% |
| Propylene Glycol | 19% |
| Dimethyl Isosorbide | 19% |

A human male subject suffering from male pattern baldness is treated by a method of this invention. Specifically, for 6 weeks, the above composition is daily administered topically to the subject.

EXAMPLE B

A composition for topical administration is made according to the method of Dowton et al., "Influence of Liposomal Composition on Topical Delivery of Encapsulated Cyclosporin A:
I. An iii vitro Study Using Hairless Mouse Skin", *S. T. P. Pharma Sciences*, Vol. 3, pp. 404–407 (1993), using [3,5-dimethyl-4-(4'-hydroxy-3'-isopropylbenzyl)phenoxy]acetic acid in lieu of cyclosporin A and using the Novasome 1 for the non-ionic liposomal formulation.

A human male subject suffering from male pattern baldness is treated each day with the above composition. Specifically, for 6 weeks, the above composition is administered topically to the subject.

EXAMPLE C

A shampoo is made, comprising:

| Component | Ex. C-1 | Ex. C-2 | Ex. C-3 |
|---|---|---|---|
| Ammonium Lauryl Sulfate | 11.5% | 11.5% | 7.5% |
| Ammonium Laureth Sulfate | 4% | 3% | 2% |
| Cocamide MEA | 2% | 2% | 2% |
| Ethylene Glycol Distearate | 2% | 2% | 2% |
| Cetyl Alcohol | 2% | 2% | 2% |
| Stearyl Alcohol | 1.2% | 1.2% | 1.2% |
| Glycerin | 1% | 1% | 1% |
| Polyquaternium 10 | 0.5% | 0.25% | — |
| Polyquaternium 24 | — | — | 0.25% |
| Sodium Chloride | 0.1% | 0.1% | 0.1% |
| Sucrose Polyesters of Cottonate Fatty Acid | 3% | 3% | — |
| Sucrose Polyesters of Behenate Fatty Acid | 2% | 3% | — |
| Polydimethyl Siloxane | — | — | 2% |
| Cocaminopropyl Betaine | — | 1% | 3% |
| Lauryl Dimethyl Amine Oxide | 1.5% | 1.5% | 1.5% |
| Decyl Polyglucose | — | — | 1% |
| DMDM Hydantoin | 0.15% | 0.15% | 0.15% |
| Minoxidil | 3% | 2% | — |
| Compound of Structure I | 3% | 5% | 6% |
| Phenoxyethanol | 0.5% | 0.5% | 0.5% |
| Fragrance | 0.5% | 0.5% | 0.5% |
| Water | q.s. | q.s. | q.s. |

A human subject suffering from male pattern baldness is treated by a method of this invention. Specifically, for 12 weeks, the above shampoo is used daily by the subject.

What is claimed is:

1. A method of treating hair loss comprising administering a composition comprising a cardiac-sparing compound characterized by the structure:

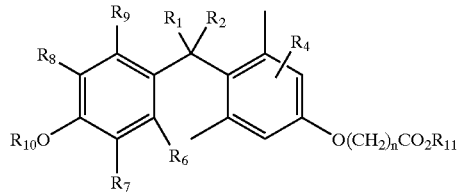

and pharmaceutically acceptable salts, hydrates, and biohydrolyzable amides, esters, and imides thereof, wherein:

n is an integer from 1 to 3;

$R_1$ and $R_2$ are each, independently, selected from the group consisting of hydrogen lower alkyl, and hydroxy; with the provisos that when $R_1$ is doubly-bonded oxygen $R_2$ is nil; and when $R_1$ is doubly-bonded sulfur $R_2$ is nil;

$R_4$ is selected from the group consisting of hydrogen, lower alkyl, and cycloalkyl;

$R_6$ and $R_9$ are each, independently, selected from the group consisting of hydrogen and lower alkyl;

$R_7$ and $R_8$ are each, independently, selected from the group consisting of hydrogen, lower alkyl, substituted phenyl and substituted benzyl, wherein the substituted phenyl and substituted benzyl may be optionally mono-, di-, or tri-substituted, independently, by a substituent selected from the group consisting of hydroxy, —COOH, lower alkyl, lower alkoxy, nitro, amino, alkytamino, dialkylamino, trifluoromethyl and cyano; with the proviso that at least one of $R_7$ and $R_8$ is not hydrogen;

$R_{10}$ is selected from the group consisting of hydrogen, lower alkyl, cycloalkyl, and acyl; and $R_{11}$ is selected from the group consisting of hydrogen, lower alkyl, and cycloalkyl.

2. A method according to claim 1 wherein $R_1$ is selected from the group consisting of methyl, hydrogen, and doubly-bonded oxygen.

3. A method according to claim 1 wherein $R_7$ is selected from the group consisting of isopropyl and hydrogen.

4. A method according to claim 1 wherein $R_6$ is selected from the group consisting of hydrogen and n-butyl.

5. A method according to claim 1 wherein $R_8$ is selected from the group consisting of hydrogen and isopropyl.

6. A method according to claim 1 wherein $R_9$ is hydrogen.

7. A method according to claim 1 wherein $R_4$ is hydrogen.

8. A method according to claim 1 wherein $R_{10}$ is selected from the group consisting of hydrogen and methyl.

9. A method according to claim 1 wherein $R_2$ is selected from the group consisting of methyl and hydrogen.

10. A method according to claim 1 wherein the administration is topical.

11. The method of claim 1, with the proviso that when one of $R_1$ and $R_2$ is hydrogen, the other is hydroxy.

* * * * *